(12) United States Patent
Lin et al.

(10) Patent No.: US 12,251,574 B2
(45) Date of Patent: Mar. 18, 2025

(54) DOSE PLANNING SYSTEM

(71) Applicant: Heron Neutron Medical Corp., Zhubei (TW)

(72) Inventors: Tzung-Yi Lin, Zhubei (TW); Yen-Wan Hsueh Liu, Zhubei (TW)

(73) Assignee: HERON NEUTRON MEDICAL CORP., Zhubei (TW)

( * ) Notice: Subject to any disclaimer, the term of this patent is extended or adjusted under 35 U.S.C. 154(b) by 445 days.

(21) Appl. No.: 17/711,400

(22) Filed: Apr. 1, 2022

(65) Prior Publication Data

US 2023/0050273 A1    Feb. 16, 2023

(30) Foreign Application Priority Data

Aug. 11, 2021   (TW) .................................. 110129618

(51) Int. Cl.
*A61N 5/10* (2006.01)

(52) U.S. Cl.
CPC ......... *A61N 5/1031* (2013.01); *A61N 5/1039* (2013.01); *A61N 2005/1034* (2013.01); *A61N 2005/109* (2013.01); *A61N 2005/1098* (2013.01)

(58) Field of Classification Search
CPC ............... A61N 5/1031; A61N 5/1039; A61N 2005/1034; A61N 2005/109; A61N 2005/1098
See application file for complete search history.

(56) References Cited

U.S. PATENT DOCUMENTS 10,080,911 B2 *  9/2018  Zankowski .......... A61N 5/1031

FOREIGN PATENT DOCUMENTS

| CN | 105120955 B | 8/2018 | |
|----|-------------|--------|------|
| CN | 110494189 A | 11/2019 | |
| CN | 112221023 A * | 1/2021 | .......... A61N 5/1031 |
| TW | I733627 B | 7/2021 | |
| TW | 202129305 A | 8/2021 | |

OTHER PUBLICATIONS

Taiwanese Office Action and Search Report for Taiwanese Application No. 110129618, dated May 10, 2022.

* cited by examiner

*Primary Examiner* — David E Smith
(74) *Attorney, Agent, or Firm* — Birch, Stewart, Kolasch & Birch, LLP

(57) ABSTRACT

A dose planning system, which takes the drug concentration distribution in human organs/tissues as well as the atomic composition distribution of human organs/tissues into consideration, and calculates the neutron/photon dose distribution in human organs/tissues under this drug concentration distribution using the Monte Carlo Method. Thereby the neutron/photon dose distribution in the organs/tissues of the human subject is calculated more accurately.

11 Claims, 4 Drawing Sheets

DOSE PLANNING SYSTEM

CROSS REFERENCE TO RELATED APPLICATIONS

This Application claims priority of Taiwan Patent Application No. 110129618, filed on Aug. 11, 2021, the entirety of which is incorporated by reference herein.

BACKGROUND OF THE INVENTION

Field of the Invention

The present disclosure relates to the field of radiation oncology, especially to a dose planning system that takes the drug concentration distribution in human organs/tissues into consideration.

Description of the Related Art

Dose planning systems that are currently known, such as a boron neutron capture therapy (BNCT) planning system, calculate and plan for the neutron/photon dose distribution based on the assumption that the drug concentration distribution is a uniform distribution. However, the concentration of boron-containing drugs in the positron emission tomography (PET) image of a human subject, for example, is not usually distributed uniformly, especially around the gross tumor volume (GTV) area. Such drug concentration distribution that are not uniformly distributed may cause the known dose planning systems to calculate and plan for the neutron/photon dose distribution inaccurately.

Therefore, there is a need for a dose planning system that is able to take the actual drug distribution in human organs/tissues into consideration, and thus to calculate and to plan for the neutron/photon dose distribution more accurately.

BRIEF SUMMARY OF THE INVENTION

An embodiment of the present disclosure provides a dose planning system, including: an image processing module, configured to load a plurality of Computer Tomography (CT) images and Region of Interest (ROI) data of a human subject, and to integrate the CT images and the ROI data, so as to generate image data; and a drug absorptance distribution module, configured to load a drug concentration distribution image of the human subject, and to perform image registration from the drug concentration distribution image to the image data, so as to generate drug absorptance distribution data that is used as a basis for the dose planning system to calculate dose distribution of drug.

In some embodiments, the dose planning system further includes: an organ/tissue distribution module, configured to locate a plurality of organs/tissues in the image data based on the ROI data, so as to generate organ/tissue distribution data; and a dose rate distribution module, configured to load the organ/tissue distribution data, the drug absorptance distribution data, and material composition data, and to calculate voxel-wise dose rate distribution in each of a plurality of homogenized volumes based on the organ/tissue distribution data, the drug absorptance distribution data, and the material composition data, so as to generate voxel-wise dose rate distribution data.

In some embodiments, the dose planning system further includes a dose planning module, configured to receive biological effectiveness parameters, the beam intensity, the drug concentration in plasma, and the irradiation time, and to integrate the biological effectiveness parameters, the beam intensity, the drug concentration in plasma, and the irradiation time into the voxel-wise dose rate distribution data, so as to generate dose planning data.

In some embodiments, the dose planning module is further configured to perform dose superposition for the multiple dose planning data that have different irradiation conditions or that are based on different image data or other radiation therapies, so as to generate multiple-dose planning data.

In some embodiments, the dose planning system further includes a dose report module, configured to generate dose report data that is capable of being visualized, wherein the dose report data includes an isodose contour, a unidimensional dose distribution, a dose-volume histogram, and statistic data of the organs and tissues.

In some embodiments, the dose rate distribution module is further configured to: set a volume homogenization size, a particle tally size, a beam parameter, and the drug concentration in plasma; perform a volume homogenization calculation and a material grouping calculation based on the organ/tissue distribution data, the drug absorptance distribution data, the material composition data, the volume homogenization size, the particle tally size, the beam parameter, and the drug concentration in plasma, so as to generate Monte Carlo calculation input data comprising a set of material grouping numbers that corresponds to each of the homogenized volumes; perform a Monte Carlo particle transport calculation based on the Monte Carlo calculation input data, so as to generate a Monte Carlo calculation output data; and calculate voxel-wise dose rate distribution in the homogenized volume based on the Monte Carlo calculation output data using a voxel dose reconstruction method, so as to generate the voxel-wise dose rate distribution data.

In some embodiments, the volume homogenization calculation includes calculating an average material composition in the homogenized volume with the volume homogenization size; and the material grouping calculation includes grouping the homogenized volumes based on the average material composition in the homogenized volumes, so as to obtain the set of material grouping numbers corresponding to each of the homogenized volumes.

In some embodiments, the average material composition includes the atomic density of each element including calcium (Ca), hydrogen (H), nitrogen (N), carbon (C), oxygen (O), phosphorus (P), and primary interaction atom of drug.

In some embodiments, the dose rate distribution module is further configured to: load the collimator description data and the beam description data; and set the beam parameter based on the collimator description data and the beam description data.

In some embodiments, the volume homogenization size is not equal to the particle tally size.

In some embodiments, calculating voxel-wise dose rate distribution in the homogenized volume using the voxel dose reconstruction method includes: generating a polynomial based on average particle fluxes of the neighboring homogenized volumes; calculating a particle flux weighting distribution in the homogenized volume using the polynomial; and calculating voxel-wise dose rate distribution in the homogenized volume based on the particle flux weighting distribution, the organ/tissue distribution data, and the drug absorptance distribution data.

BRIEF DESCRIPTION OF THE DRAWINGS

The present disclosure can be more fully understood by reading the subsequent detailed description and examples with references made to the accompanying drawings, wherein.

DETAILED DESCRIPTION OF THE INVENTION

Figure 1:
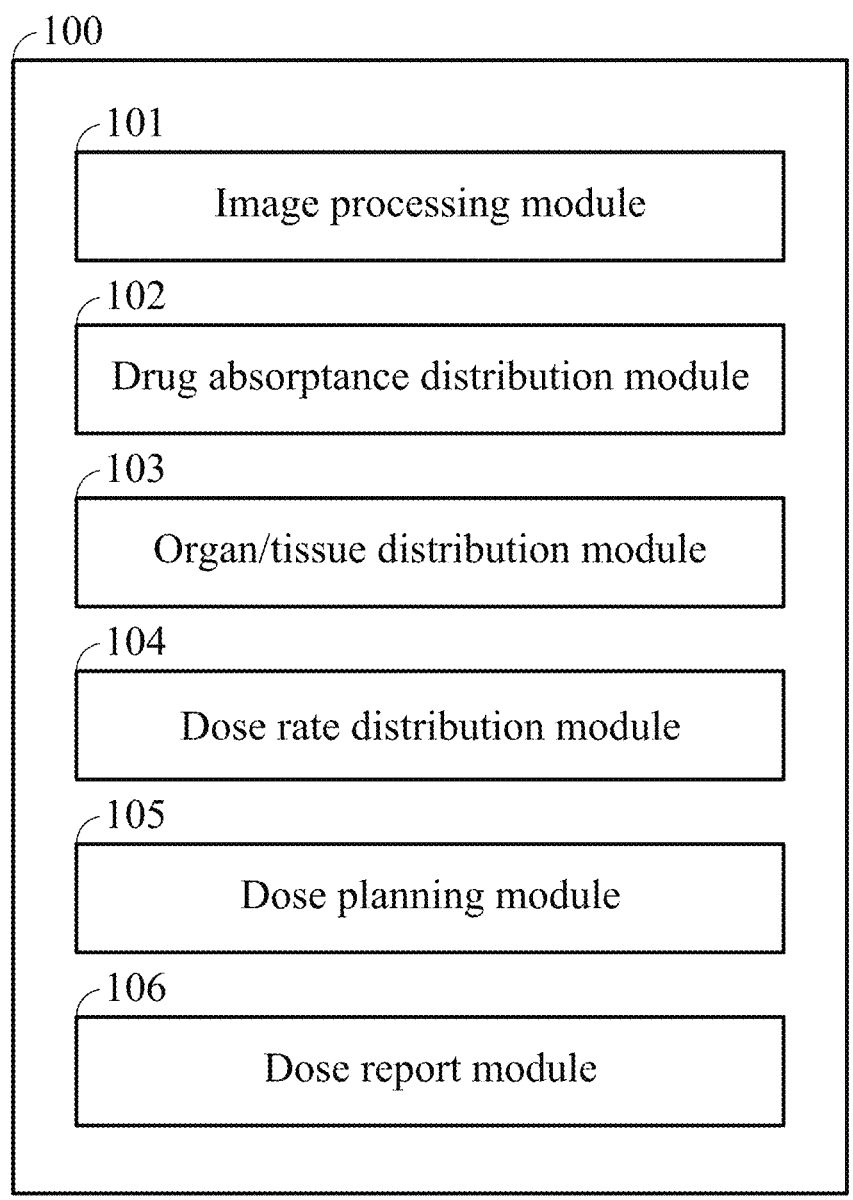
FIG. 1 is the system block diagram of a dose planning system, according to an embodiment of the present disclosure.

FIG. 1 is the system block diagram of a dose planning system 100, according to an embodiment of the present disclosure. As shown in FIG. 1, the dose planning system 100 includes an image processing module 101, a drug absorptance distribution module 102, an organ/tissue distribution module 103, a dose rate distribution module 104, a dose planning module 105, and a dose report module 106.

The dose planning system 100 further includes at least one processor. The dose planning system 100 may load a program for the processor(s) to execute the functions of the image processing module 101, the drug absorptance distribution module 102, the organ/tissue distribution module 103, the dose rate distribution module 104, the dose planning module 105, and the dose report module 106. The dose planning system 100 may also include at least one input device (e.g., a mouse, a keyboard, a controller, a touch panel element, or a keyboard) and at least one output device (e.g., a displaying device, a printer, or a speaker). The dose planning system 100 may also include one or more storage devices for storing data, such as disk drives, optical storage devices, or solid-state storage devices like random access memory (RAM), read-only memory (ROM), removable media devices, memory cards, and flash memory cards.

The image processing module 101 in FIG. 1 may be configured to load a plurality of Computer Tomography (CT) images and Region of Interest (ROI) data of a human subject, and to integrate the CT images and the ROI data, so as to generate image data. The CT images are two-dimensional (2D) images of specific scanning areas such as the head, the chest, and the abdomen of the human subject that are taken using many X-rays to penetrate the human body from different angles and then composed by a computer. The CT images are used for observing the inner body of the human subject. The image data is a three-dimensional (3D) image formed by stacking up multiple 2D CT images, and is used for depicting the locations of one or more ROIs in the body of the human subject. The ROI data includes the coordinates of multiple points in each ROI, and is used for drawing the contour of each ROI. An ROI may be, for example, a tumor or a specific organ. However, which organ the ROI is and whether the ROI is a tumor are not defined in the image data.

The drug absorptance distribution module 102 in FIG. 1 may be configured to load a drug concentration distribution image of the human subject, and to perform image registration on the drug concentration distribution image and the image data, so as to generate drug absorptance distribution data that is used for depicting the relative drug absorptance in the body of the human subject. The drug concentration distribution image is a positron emission tomography (PET) image or a magnetic resonance imaging (MRI) image used for depicting the drug concentration distribution in the human subject. The image registration described herein can be any intensity-based medical image registration algorithm that maps the data in an image (i.e., the data in the drug concentration distribution image, according to an embodiment of the present disclosure) to a space coordinate system of the image data, but the embodiment of the present disclosure is not limited hereto.

The organ/tissue distribution module 103 in FIG. 1 may locate a plurality of organs/tissues in the image data based on the ROI data, so as to generate organ/tissue distribution data that is used for depicting the distribution of locations of the plurality of organs/tissues in the human subject. The organs/tissues may be tumors or specific organs. The method for localizing the organs/tissues may be to automatically generate the correspondence between each organ/tissue and the area they are located in (e.g., the first area corresponds to the brain, the second area corresponds to a tumor, and so on) using artificial intelligence (AI) technology, or to provide a graphic tool on the user interface that allows users to contour and label the organs/tissues manually.

Figure 2:
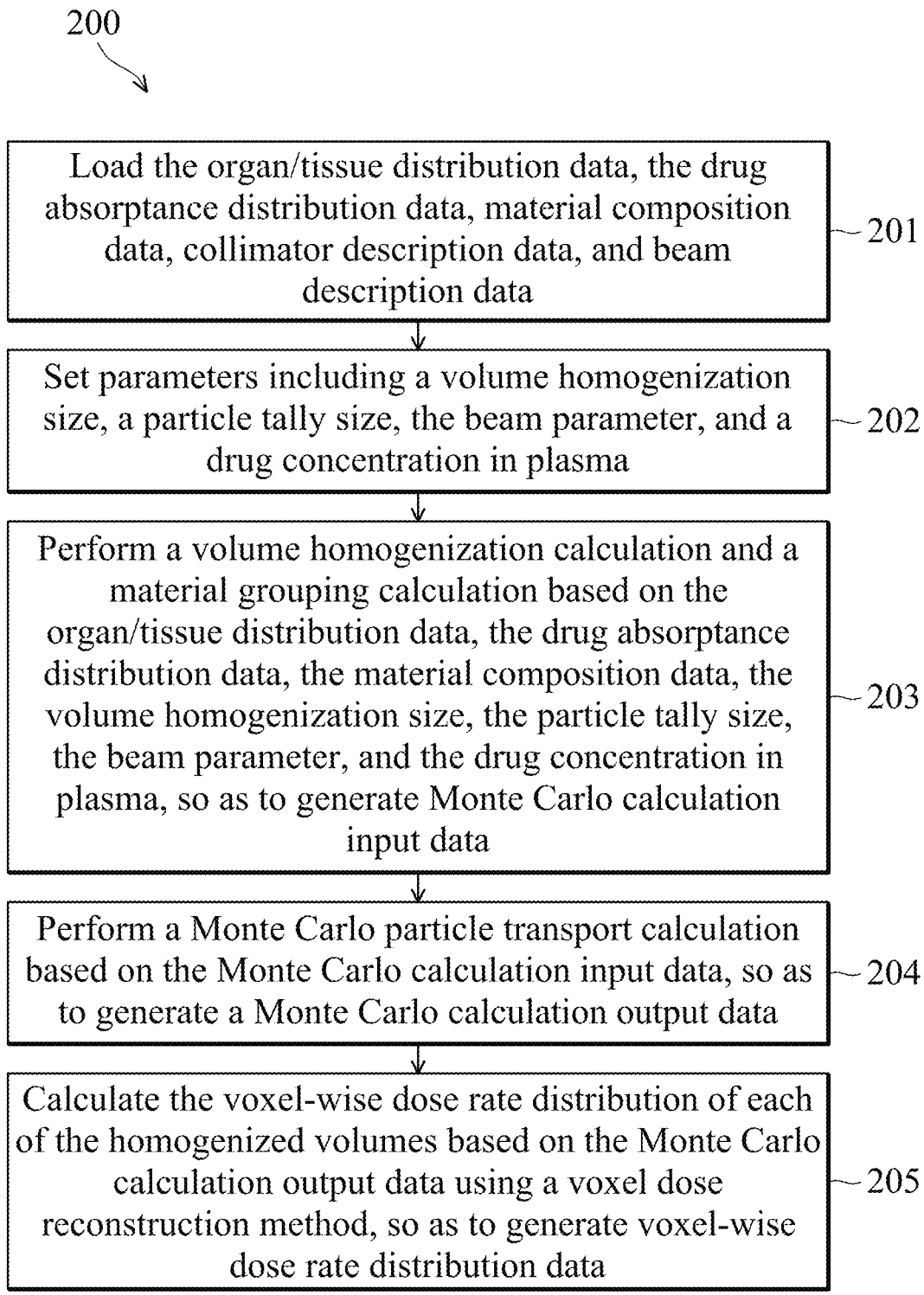
FIG. 2 illustrates the flow diagram of a process that is configured to be executed by the dose rate distribution module in FIG. 1; and FIG. 3A, FIG. 3B.

FIG. 2 illustrates the flow diagram of a process 200 that is configured to be executed by the dose rate distribution module 104 in FIG. 1. As shown in FIG. 2, the process 200 includes steps 201-205.

The process 200 begins at step 201. At step 201, the organ/tissue distribution data, the drug absorptance distribution data, material composition data, collimator description data, and beam description data are loaded. The material composition data described herein records the composition of elements such as calcium (Ca), hydrogen (H), nitrogen (N), carbon (C), oxygen (O), and phosphorus (P) of each organ/tissue in human body. The collimator description data and the beam description data respectively records the parameters that depicts the conditions of the collimator and the beam. And then, the process 200 proceeds to step 202.

At step 202, parameters including a volume homogenization size, a particle tally size, the beam parameter, and a drug concentration in plasma are set based on the collimator description data and the beam description data. These parameters are used as input parameters that are required for executing the next step (i.e., step 203). The volume homogenization size and the particle tally size are in the unit of pixels (e.g., n×m pixels). In some embodiments, the volume homogenization size and the particle tally size are set to be unequal. After step 202 ends, the process 200 proceeds to step 203.

At step 203, a volume homogenization calculation and a material grouping calculation are performed based on the organ/tissue distribution data, the drug absorptance distribution data, the material composition data, the volume homogenization size, the particle tally size, the beam parameter, and the drug concentration in plasma, so as to generate Monte Carlo calculation input data that is used as an input data that is required for executing the next step (i.e., step 204). The Monte Carlo calculation input data includes a set of material grouping numbers that corresponds to each of the homogenized volumes. And then, the process 200 proceeds to step 204.

In some embodiments, the volume homogenization calculation includes calculating the average material composition in each homogenized volumes with the volume homogenization size set at step 203. For example, assuming that the original resolution of the CT image of the human subject is 512×512 pixels, and the volume homogenization size set at step 203 is n×m pixels, then the average material composition in each of the n×m homogenized volumes is calculated. The average material composition may include an atomic density of each element including calcium (Ca), hydrogen (H), nitrogen (N), carbon (C), oxygen (O), phosphorus (P), and primary interaction atom of drug.

In some embodiments, the material grouping calculation includes grouping the homogenized volumes based on the average material composition in the homogenized volumes, so as to obtain the set of material grouping numbers corresponding to each of the homogenized volumes. Compared to the homogenized volumes in different groups, the homogenized volumes in the same group have more similar proportional distribution of the average material composition (e.g., more similar percentage of the atomic density of elements including calcium (Ca), hydrogen (H), nitrogen (N), carbon (C), oxygen (O), phosphorus (P), and primary interaction atom of drug).

At step 204, a Monte Carlo particle transport calculation is performed based on the Monte Carlo calculation input data, so as to generate a Monte Carlo calculation output data. And then, the process 200 proceeds to step 205.

At step 205, the voxel-wise dose rate distribution of each of the homogenized volumes is calculated based on the Monte Carlo calculation output data using a voxel dose reconstruction method, so as to generate voxel-wise dose rate distribution data. The voxel-wise dose rate distribution data is used for depicting the distribution of the voxel-wise dose rate in the homogenized volumes.

In some embodiments, using the voxel dose reconstruction method to calculate voxel-wise dose rate distribution in each of the homogenized volumes includes generating a second-order polynomial (alternatively a single-order polynomial, or an exponential polynomial) based on average particle fluxes of the neighboring homogenized volumes, and calculating a particle flux weighting distribution in the homogenized volume using the polynomial. Finally, the dose rate of each voxel is calculated based on the particle flux weighting distribution, the organ/tissue distribution data, and the drug absorptance distribution data.

The dose planning module 105 in FIG. 1 may be further configured to receive the biological effectiveness parameters, the beam intensity, the drug concentration in plasma, and the irradiation time, and to integrate the biological effectiveness parameters, the beam intensity, the drug concentration in plasma, and the irradiation time into the voxel-wise dose rate distribution data, so as to generate dose planning data.

In some embodiments, the dose planning module 105 in FIG. 1 may be further configured to perform dose superposition for a multitude of dose planning data that have different irradiation conditions or that are based on different image data or other radiation therapies, so as to generate multiple-dose planning data.

In some embodiments, the dose report module 106 in FIG. 1 may be configured to generate dose report data that is capable of being visualized based on the dose planning data. The dose report data may include an isodose contour, a unidimensional dose distribution, a dose-volume histogram, and statistic data of the organs and tissues.

Figure 3B:
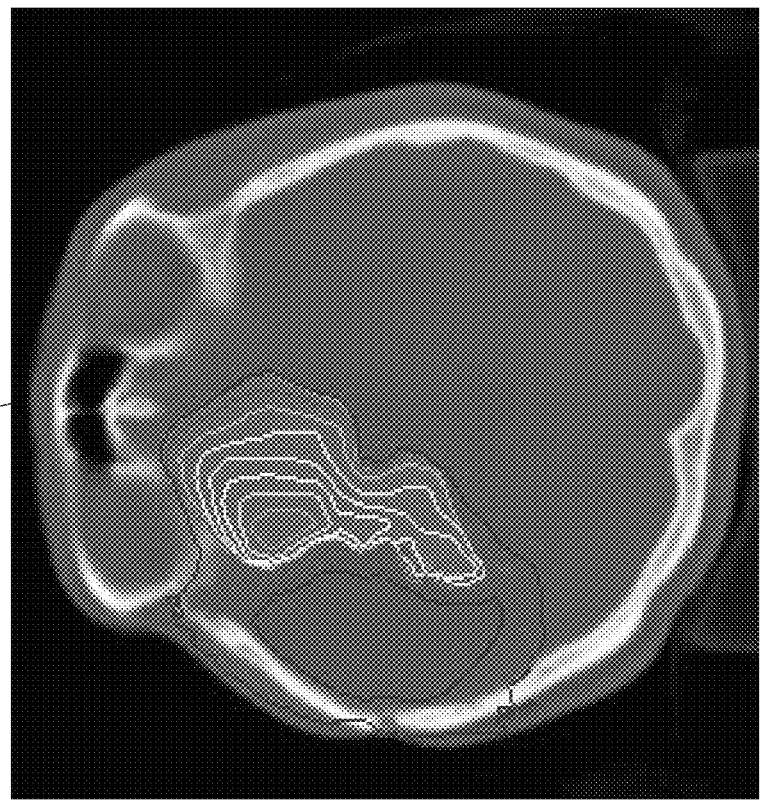
FIG. 3C shows the difference between the dose distribution calculated by the dose planning system of the present disclosure and the known art.
Figure 3A:
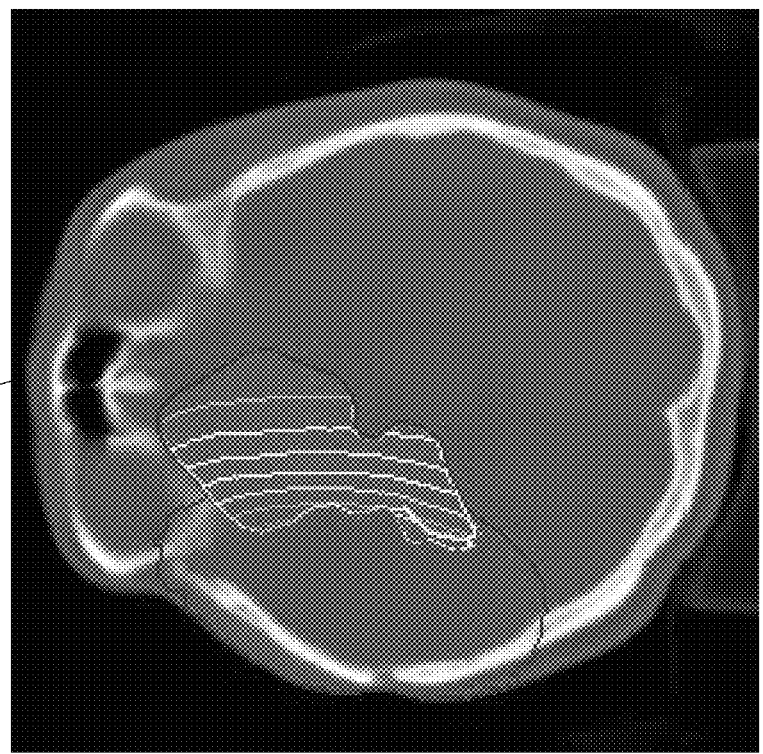
Figure 3C:
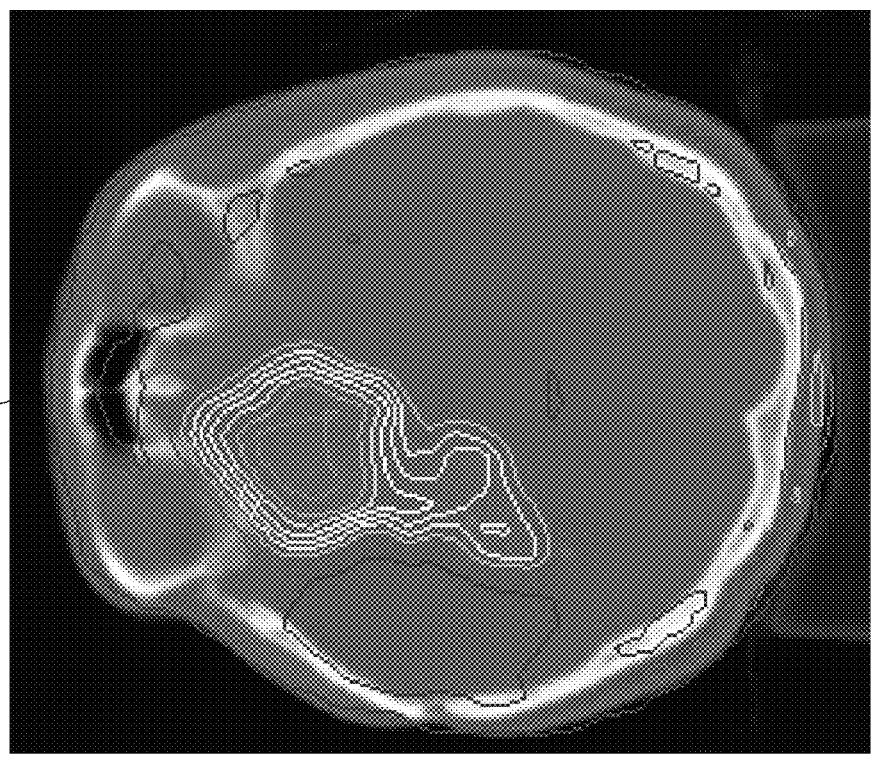

FIG. 3A, FIG. 3B, and FIG. 3C shows the difference between the dose distribution calculated by the dose planning system of the present disclosure and the known art. The isodose contour 301 in FIG. 3A is an exemplary isodose contour that is generated using the known art thereby the drug concentration in the organs/tissues of the human subject is set as a fixed value. FIG. 3B shows an exemplary isodose contour 302 that is generated based on the drug isoconcentration contour 303 of FIG. 3C by the dose planning system according to an embodiment of the present disclosure. In this example, it is assumed that the beam comes from the left of the image. The lines of the isodose contour 301, the isodose contour 302, and the drug isoconcentration contour diagram 303 are drawn in red, orange, yellow, green, and blue, to indicate values from high to low. As shown in FIG. 3A, the isodose contour 301 shows that the dose distribution gradually decreases from the left to the right, which is similar to the neutron flux distribution of a beam combing from the left. In contrast, the isodose contour 302 resulted from taking the drug concentration distribution into consideration, as shown in FIG. 3B, shows that the dose distribution is more reasonable than the dose distribution of the isodose contour 301 which gradually decreases from the left to the right.

The dose planning system takes the actual drug distribution in the organs/tissues of the human subject into consideration, and thereby calculates the neutron/photon dose distribution in the organs/tissues of the human subject more accurately, and facilitates more adequate dose planning.

Ordinal terms used in the claims, such as "first," "second," "third," etc., are used to modify the elements appearing in the claims, and do not imply any prioritization, precedence relation, or a component is higher than the other component, or the chronological order in which the method steps are performed. The intention is to make a distinction between elements with the same name.

"Some embodiments", "an embodiment", "embodiment", "multiple embodiments", "this embodiment", "these embodiments", "one or more embodiments", "some of the embodiments" and "one embodiment" all mean one or more embodiments (but not all), unless otherwise specifically defined.

The above paragraphs are described with multiple aspects. Obviously, the teachings of the specification may be performed in multiple ways. Any specific structure or function disclosed in examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A dose planning system, comprising:
   an image processing module, configured to load a plurality of Computer Tomography (CT) images and Region of Interest (ROI) data of a human subject, and to integrate the CT images and the ROI data, so as to generate image data; and
   a drug absorptance distribution module, configured to load a drug concentration distribution image of the human subject, and to perform image registration from the drug concentration distribution image to the image data, so as to generate drug absorptance distribution data that is used as a basis for the dose planning system to calculate dose distribution of drug.

2. The dose planning system as claimed in claim 1, further comprising:
an organ/tissue distribution module, configured to locate a plurality of organs/tissues in the image data based on the ROI data, so as to generate organ/tissue distribution data; and
a dose rate distribution module, configured to load the organ/tissue distribution data, the drug absorptance distribution data, and material composition data, and to calculate voxel-wise dose rate distribution in each of a plurality of homogenized volumes based on the organ/tissue distribution data, the drug absorptance distribution data, and the material composition data, so as to generate voxel-wise dose rate distribution data.

3. The dose planning system as claimed in claim 2, further comprising:
a dose planning module, configured to receive biological effectiveness parameters, a beam intensity, a drug concentration in plasma, and an irradiation time, and to integrate the biological effectiveness parameters, the beam intensity, the drug concentration in plasma, and the irradiation time into the voxel-wise dose rate distribution data, so as to generate dose planning data.

4. The dose planning system as claimed in claim 3, wherein the dose planning module is further configured to perform dose superposition for a multitude of dose planning data that have different irradiation conditions or that are based on different image data or other radiation therapies, so as to generate multiple-dose planning data.

5. The dose planning system as claimed in claim 3, further comprising:
a dose report module, configured to generate dose report data that is capable of being visualized based on the dose planning data, wherein the dose report data comprises an isodose contour, a unidimensional dose distribution, a dose-volume histogram, and statistic data of the organs and tissues.

6. The dose planning system as claimed in claim 2, wherein the dose rate distribution module is further configured to:
set a volume homogenization size, a particle tally size, a beam parameter, and the drug concentration in plasma;
perform a volume homogenization calculation and a material grouping calculation based on the organ/tissue distribution data, the drug absorptance distribution data, the material composition data, the volume homogenization size, the particle tally size, the beam parameter, and the drug concentration in plasma, so as to generate Monte Carlo calculation input data comprising a set of material grouping numbers that corresponds to each of the homogenized volumes;
perform a Monte Carlo particle transport calculation based on the Monte Carlo calculation input data, so as to generate a Monte Carlo calculation output data; and
calculate voxel-wise dose rate distribution in the homogenized volume based on the Monte Carlo calculation output data using a voxel dose reconstruction method, so as to generate the voxel-wise dose rate distribution data.

7. The dose planning system as claimed in claim 6, wherein the volume homogenization calculation comprises calculating an average material composition in the homogenized volume with the volume homogenization size; and
wherein the material grouping calculation comprises grouping the homogenized volumes based on the average material composition in the homogenized volumes, so as to obtain the set of material grouping numbers corresponding to each of the homogenized volumes.

8. The dose planning system as claimed in claim 7, wherein the average material composition comprises an atomic density of each element including calcium (Ca), hydrogen (H), nitrogen (N), carbon (C), oxygen (O), phosphorus (P), and primary interaction atom of drug.

9. The dose planning system as claimed in claim 6, wherein the dose rate distribution module is further configured to:
load collimator description data and beam description data; and
set the beam parameter based on the collimator description data and the beam description data.

10. The dose planning system as claimed in claim 6, wherein the volume homogenization size is not equal to the particle tally size.

11. The dose planning system as claimed in claim 6, wherein calculating voxel-wise dose rate distribution in the homogenized volume using the voxel dose reconstruction method comprises:
generating a polynomial based on average particle fluxes of the neighboring homogenized volumes;
calculating a particle flux weighting distribution in the homogenized volume using the polynomial; and
calculating voxel-wise dose rate distribution in the homogenized volume based on the particle flux weighting distribution, the organ/tissue distribution data, and the drug absorptance distribution data.

* * * * *